US00PP25747P3

(12) United States Plant Patent
Kibbe et al.

(10) Patent No.: US PP25,747 P3
(45) Date of Patent: Jul. 28, 2015

(54) STRAWBERRY PLANT NAMED 'DRISSTRAWFORTY'

(50) Latin Name: *Fragaria×ananassa*
Varietal Denomination: DrisStrawForty

(71) Applicant: DRISCOLL STRAWBERRY ASSOCIATES, INC., Watsonville, CA (US)

(72) Inventors: Esther Kibbe, Seffner, FL (US); Philip J. Stewart, Watsonville, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 129 days.

(21) Appl. No.: 13/998,150

(22) Filed: Oct. 7, 2013

(65) Prior Publication Data

US 2015/0101090 P1 Apr. 9, 2015

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Susan McCormick Ewoldt
(74) *Attorney, Agent, or Firm* — Jondle & Associates, P.C.

(57) ABSTRACT

A new and distinct variety of strawberry plant named 'DrisStrawForty' particularly characterized by a vigorous plant bearing dark red, glossy fruit having a mid-season harvest maturity is disclosed.

3 Drawing Sheets

Genus and species: *Fragaria×ananassa.*
Variety denomination: 'DrisStrawForty'.

BACKGROUND OF THE NEW PLANT

The present invention relates to a new and distinct strawberry variety designated 'DrisStrawForty' and botanically known as *Fragaria×ananassa*. This new strawberry variety was discovered in Hillsborough County, Calif. in February 2008 and originated from a cross between the proprietary female parent '44N314' (unpatented) and the proprietary male parent '227M226' (unpatented). A single plant was selected for asexual propagation via tissue culture and vegetative cuttings in Shasta County, Calif. in 2008.

'DrisStrawForty' underwent further testing in Ventura County, Calif. for five years (2008-2012). The present invention has been found to retain its distinctive characteristics through successive asexual propagations via stolons and tissue culture.

Plant Breeder's Rights for this variety have not been applied for. 'DrisStrawForty' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Ventura County, Calif.

1. Vigorous plant;
2. Dark red, glossy fruit; and
3. Mid-season harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from six-month-old plants.

DESCRIPTION OF THE NEW VARIETY

Figure 1:
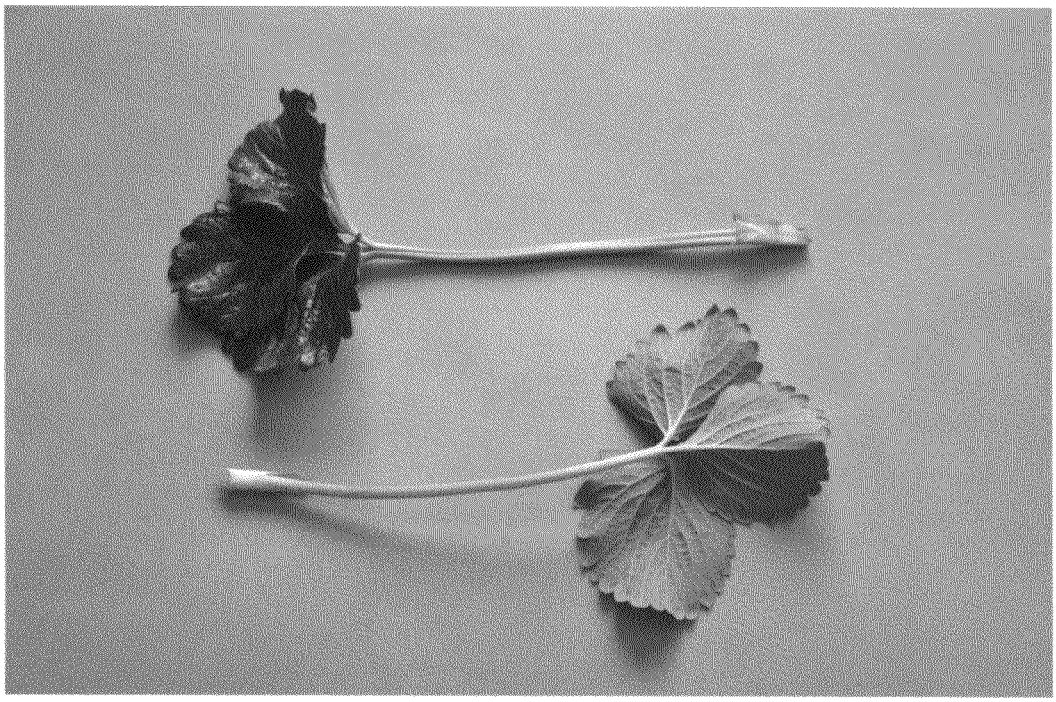
FIG. 1 shows upper and lower surfaces of the leaves of the plant with three leaflets.
Figure 2:
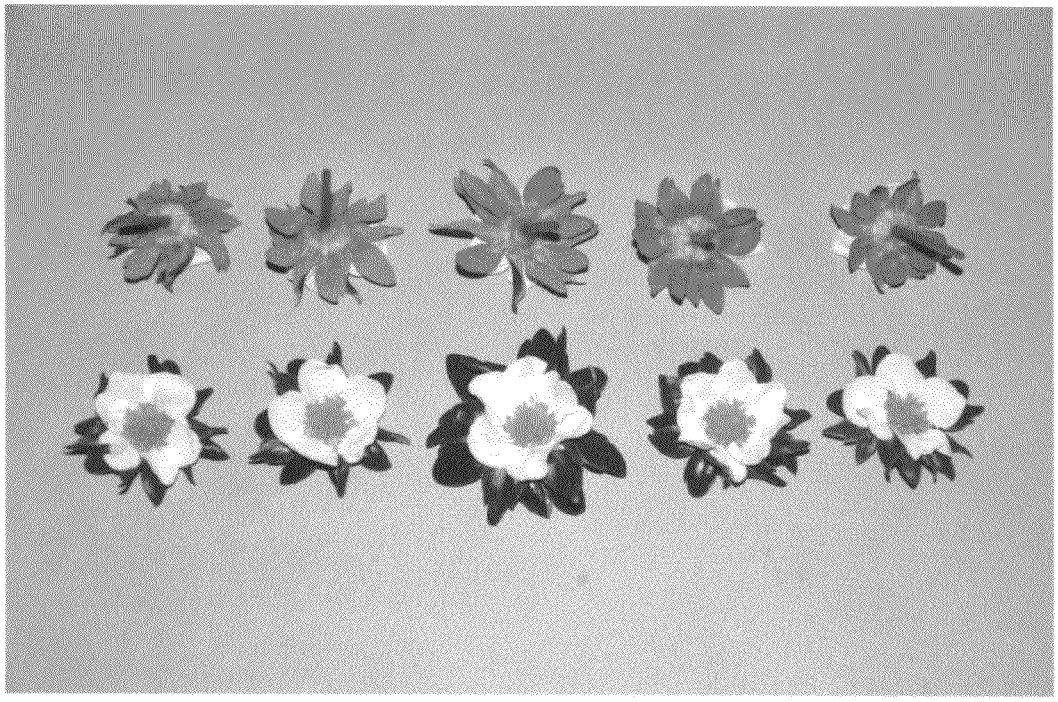
FIG. 2 shows both upper and lower surfaces of the flowers.
Figure 3:
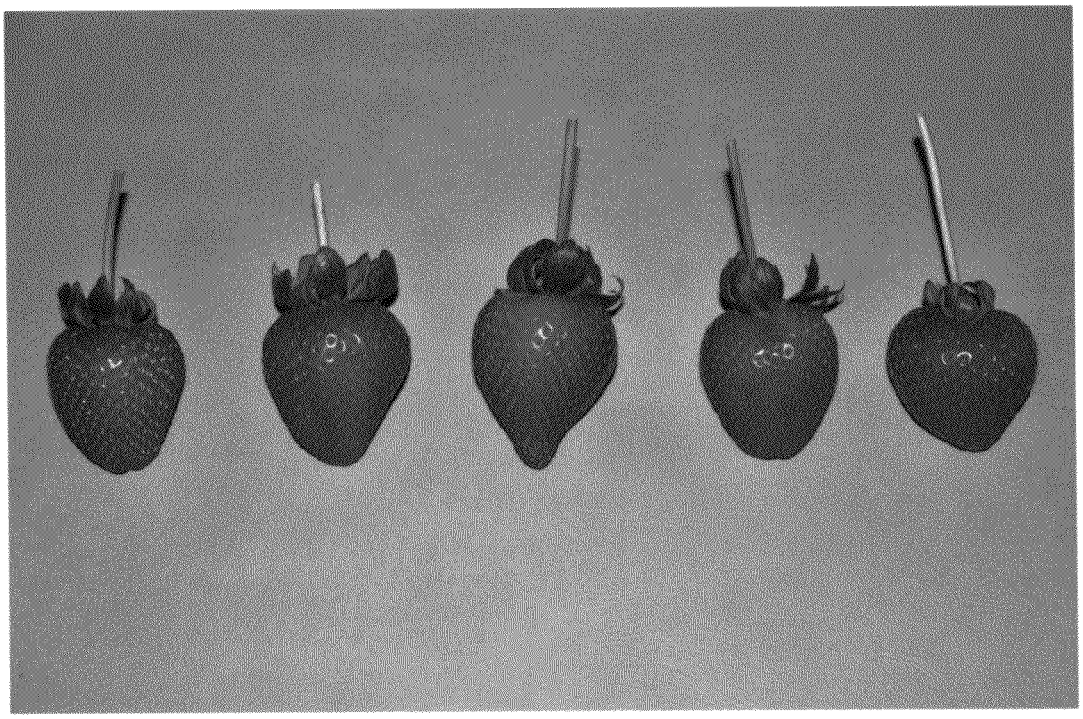
FIG. 3 shows the whole fruit.
Figure 4:
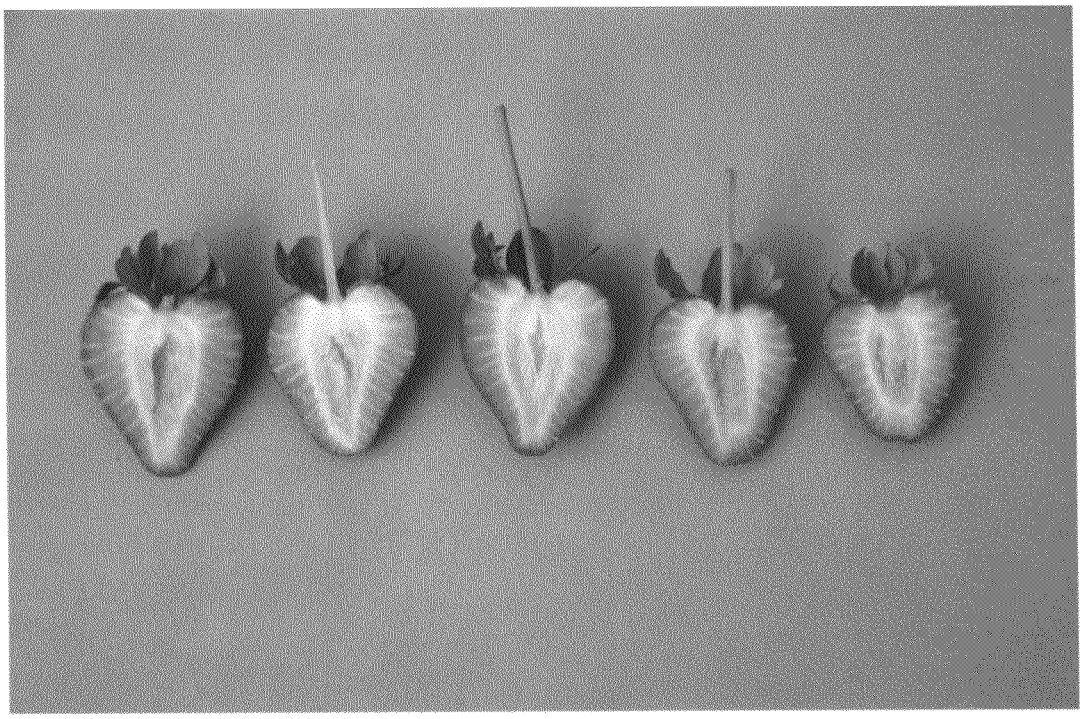
FIG. 4 shows the fruit in longitudinal cross-section.
Figure 5:
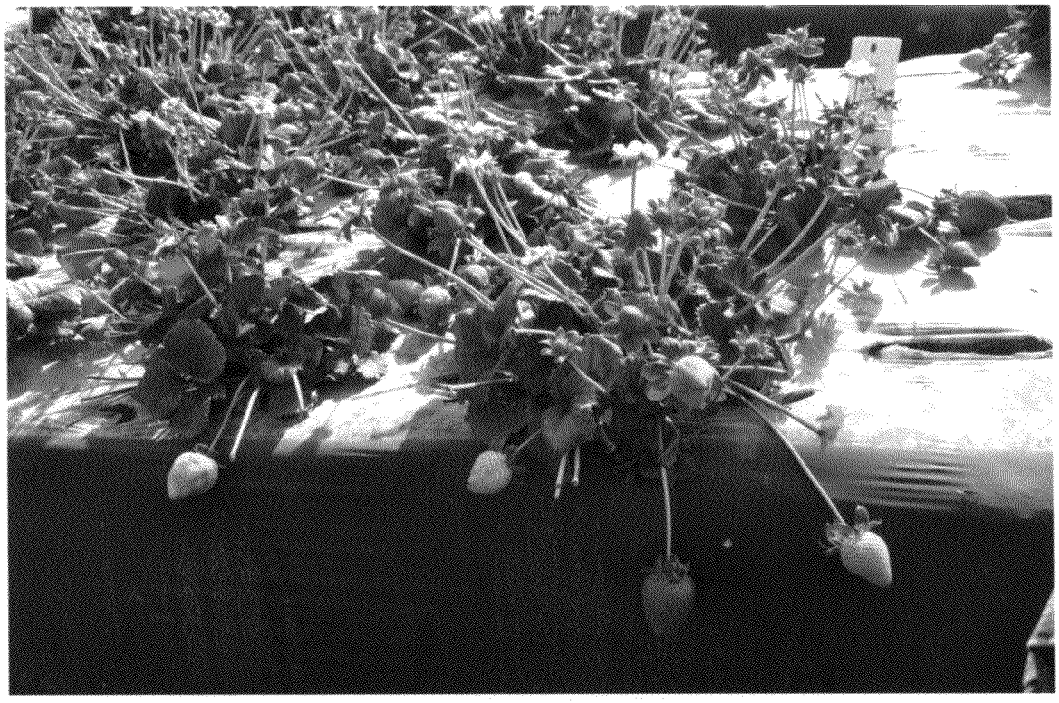
FIG. 5 shows the whole plant.

The following detailed descriptions set forth the distinctive characteristics of 'DrisStrawForty'. The data which define these characteristics is based on observations taken in Ventura County, Calif. from 2008 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawForty' has not been observed under all possible environmental conditions. The botanical description of 'DrisStrawForty' was taken from six-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawForty'.

Parentage:

*Female parent*.—The proprietary variety '44N314' (unpatented).

*Male parent*.—The proprietary variety '227M226' (unpatented).

Plant:

*Height*.—24.2 cm.

*Diameter*.—39.9 cm.

*Number of crowns/plant*.—2.

*Habit*.—Flat — spreading.

*Density of individual plant*.—Medium.

*Vigor* (*health and hardiness of plant*).—Strong.

Terminal leaflets:

*Size*.—Small. Length: 5.4 cm. Width: 5.0 cm. Length/width ratio: 1.1 (Longer than broad).

*Number of teeth/terminal leaflet*.—20.

*Shape of teeth*.—Rounded — crenate.

*Color*.—Upper surface: RHS 137B (Dark green). Lower surface: RHS 148B (Medium yellow-green).

*Shape in cross section*.—Concave.

*Blistering*.—Medium.

*Glossiness*.—Strong.

*Number of leaflets*.—Three only.

*Shape*—Orbicular.

*Base shape*.—Rounded.

*Apex descriptor*.—Rounded.

*Variegation*.—Absent.

*Margin*.—Crenate.

*Margin profile*.—Flat.

Petiole:

*Length*.—Medium; 11.5 cm.

*Diameter*.—2.65 mm.

*Pubescence*.—Dense.

*Pose of hairs*.—Slightly upwards and outwards — horizontal.

*Color*.—RHS 145A (Medium yellow-green).

*Bract frequency*.—0.

Petiolule:

*Length*.—6.20 mm.

*Diameter*.—1.44 mm.

*Color*.—RHS 145A (Medium yellow-green).

Stipule:

*Length*.—2.5 cm.

*Width*.—7.73 mm.

*Pubescence*.—Dense.

*Stipule anthocyanin coloration*.—Absent or very weak; RHS 185B (Medium greyed-purple).

Inflorescence:

*Position relative to foliage*.—Above.

*Number of flowers*.—Many.

*Time of flowering* (*50% of plants at first flower*).—Medium.

*Flowering interval*.—Mid-November to late March.

*Flower size*.—Large.

*Diameter*.—32.24 mm.

*Number of flowers per plant*.—37.4.

*Petals*.—Shape: Orbicular. Apex: Rounded. Base: Concavo-convex. Margin: Entire. Spacing: Overlapping. Length: 15.42 mm. Width: 17.26 mm. Length/width ratio: 0.9 (Broader than long). Petal number per flower: 6. Color (upper surface): RHS NN155D (White).

*Calyx*.—Diameter: 41.79 mm. Diameter relative to corolla: Larger. Inner calyx diameter relative to outer: Same size. Insertion of calyx: Level. Pose of calyx segments: Reflexed — upwards. Size of calyx in relation to fruit: Slightly larger. Adherence of calyx: Strong.

*Sepal*.—Shape: Elliptical. Apex: Convex. Margin: Entire. Length: 17.07 mm. Width: 8.11 mm. Sepal number: 13.

*Receptacle color*.—RHS N144A (Medium yellow-green).

*Stamen*.—Present. Anther color: RHS N163C (Medium greyed-orange).

*Pedicel*.—Attitude of hairs: Upwards.

Fruiting truss:

*Length*.—Medium; 21.6 cm.

*Diameter at base of truss*.—3.35 mm.

*Number of berries per fruiting truss*.—2.

*Attitude at first picking*.—Erect.

*Color at base of truss*.—RHS 145A (Medium yellow-green).

Fruit:

*Relative fruit size*.—Medium.

*Length*.—47.61 mm.

*Width*.—41.40 mm.

*Length/width ratio*.—1.2 (Longer than broad).

*Fruit weight*.—27.3 g.

*Fruit hollow length*.—19.04 mm.

*Fruit hollow width*.—11.49 mm.

*Fruit hollow length/width ratio*.—1.7 (Longer than broad).

*Fruit hollow center* (*cavity*).—Medium.

*Predominant fruit shape*.—Conical.

*Difference in shape between primary and secondary fruits*.—None or very slight.

*Evenness of fruit surface*.—Slightly uneven.

*Fruit skin color*.—RHS 53A (Dark red).

*Evenness of fruit color*.—Even or very slightly uneven.

*Fruit glossiness*.—Strong.

*Achenes*.—Insertion of achenes: Level. Coloration (sunward side of berry): RHS 184B (Medium greyed-purple). Coloration (shaded side of berry): RHS 144A (Medium yellow-green). Number per berry: 346. Weight (weight of achenes divided by total # seed): 0.000594364 g. Width of band without achenes: Absent or very narrow.

*Firmness of flesh* (*when fully ripe*).—Firm.

*Color of flesh* (*excluding core*).—RHS 45A (Dark red) and RHS N155D (White).

*Color of core*.—RHS 37B (Light red).

*Evenness of flesh color*.—Slightly uneven.

*Distribution of flesh color*.—Marginal and central.

*Sweetness*.—Medium.

*Acidity*.—Medium.

*Texture when tasted*.—Medium.

*Type of bearing*.—Not everbearing — not remontant.

*Harvest interval*.—Mid-December to early April.

*Harvest maturity*.—Mid-season.

*Production per plant*.—843 g.

Disease and pest resistance: Data not available.

COMPARISON WITH PARENTAL AND COMMERCIAL VARIETIES

When 'DrisStrawForty' is compared to the female parent '44N314' (unpatented), 'DrisStrawForty' has more vigorous plants and later fruit production with smaller fruit size than '44N314'.

When 'DrisStrawForty' is compared to the male parent '227M226' (unpatented), 'DrisStrawForty' has more vigorous plants and later fruit production with better shelf life than '227M226'.

When 'DrisStrawForty' is compared to the commercial variety 'DrisStrawTwelve' (U.S. Plant Pat. No. 21,538), 'DrisStrawForty' has strongly glossy leaves, large flowers and inflorescence positioned above the foliage, whereas 'DrisStrawTwelve' has weakly glossy leaves, medium sized flowers and inflorescence positioned beneath the foliage. Additionally, 'DrisStrawForty' has medium sized, strongly glossy fruit, whereas 'DrisStrawTwelve' has large, medium glossy fruit.

When 'DrisStrawForty' is compared to the commercial variety 'DrisStrawTwentyFour' (U.S. Plant Pat. No. 23,378), 'DrisStrawForty' has small, strongly glossy terminal leaflets and inflorescence positioned above the foliage, whereas 'DrisStrawTwentyFour' has medium sized, medium glossy terminal leaflets and inflorescence positioned beneath the foliage. Additionally, 'DrisStrawForty' has medium sized fruit with a medium hollow center, whereas 'DrisStrawTwentyFour' has very large fruit with a large hollow center.

We claim:

1. A new and distinct variety of strawberry plant named 'DrisStrawForty' as described and shown herein.

* * * * *